United States Patent [19]

Hall, Sr.

[11] 4,108,164

[45] Aug. 22, 1978

[54] STANDARD BENDING PROFILE JACKET

[76] Inventor: Henry W. Hall, Sr., 941 Avon Rd., West Palm Beach, Fla. 33401

[21] Appl. No.: 728,632

[22] Filed: Oct. 1, 1976

[51] Int. Cl.² .............................................. A61B 5/10
[52] U.S. Cl. ................................... 128/25; 33/174 D
[58] Field of Search ................ 128/2 N, 2 S; 3/1.1; 340/279; 33/174 D, 174 L; 338/86, 94, 44, 151

[56] References Cited

U.S. PATENT DOCUMENTS

| | | | |
|---|---|---|---|
| 1,342,594 | 6/1920 | Parkin, Jr. ............... | 338/151 |
| 1,553,766 | 9/1925 | Friedrich ................. | 338/151 |
| 2,893,134 | 7/1959 | Shea et al. ............... | 33/206 |
| 3,236,230 | 2/1966 | Follett .................... | 128/2.05 A |
| 3,268,845 | 8/1966 | Whitmore ................ | 128/2 S |
| 3,589,021 | 6/1971 | Hall ....................... | 33/207 R |
| 3,608,541 | 9/1971 | Hall ....................... | 340/279 |
| 3,908,279 | 9/1975 | Yoslow et al. ........... | 128/2 S |
| 3,937,212 | 2/1976 | Fletcher et al. .......... | 33/174 D |
| 3,955,562 | 5/1976 | Farrar, Jr. ................ | 128/2 S |

FOREIGN PATENT DOCUMENTS

| | | | |
|---|---|---|---|
| 1,383,594 | 2/1975 | United Kingdom ...... | 128/2 S |
| 178,029 | 1/1965 | U.S.S.R. .................. | 128/2 S |
| 231,711 | 11/1968 | U.S.S.R. .................. | 128/2 S |
| 302,103 | 4/1971 | U.S.S.R. .................. | 128/2 S |

OTHER PUBLICATIONS

"A Simple Goniometric System and Its Testing" - Trnkoczy et al., IEEE Trans on Biomed Engr. 5/75, pp. 257-259.

"A Simple Method for Recording Achilles Tendon Reflexes" - Lancet 2/16/63, p. 363.

"An Electrogoniometer for the Finger" - Thomas, D. H. et al.; Amer. Jrnl. Med. Electronics, Apr.-Jun. 1964, pp. 96-100.

"A Combined Flexi-Rule/Hydrogoniometer for Measurement of Lumbar Spine & Sagittal Movement"- Anderson, J.A.D. et al., Jrnl. Rheum. and Rehab.; V.14, 1975, pp.173-179.

*Primary Examiner*—Robert W. Michell
*Assistant Examiner*—Francis J. Jaworski
*Attorney, Agent, or Firm*—Berman, Aisenberg & Platt

[57] ABSTRACT

A jacket which functions as a measurement tool for providing information regarding the flexural conduct of the wearer. The jacket has a plurality of self-contained electrical measurement devices mounted thereon, each of which is designed to measure the angle of tilt of a particular portion of the spine in an act of leaning. In a preferred embodiment, the jacket has three clinometer frames which project through slots formed in the rear of the jacket so as to be positioned adjacent the sacrum, lumbar and thoracic portions of the spine. Mounted in each clinometer is an electrical measurement device which responds to changes in its axial angle to vary its electrical output signal proportionately. In a preferred embodiment, the electrical measurement device comprises a gravity-actuated potentiometer which utilizes a movable mercury contact as an angle sensing means. Each clinometer is individually powered and has its output response fed to a gauge which may be easily visually observed by the wearer. In lieu of gauge readings, the response of the potentiometers may be fed to a pen recorder to provide a permanent record of he dynamics of the entire flexural process.

26 Claims, 12 Drawing Figures

U.S. Patent  Aug. 22, 1978  Sheet 1 of 3  4,108,164
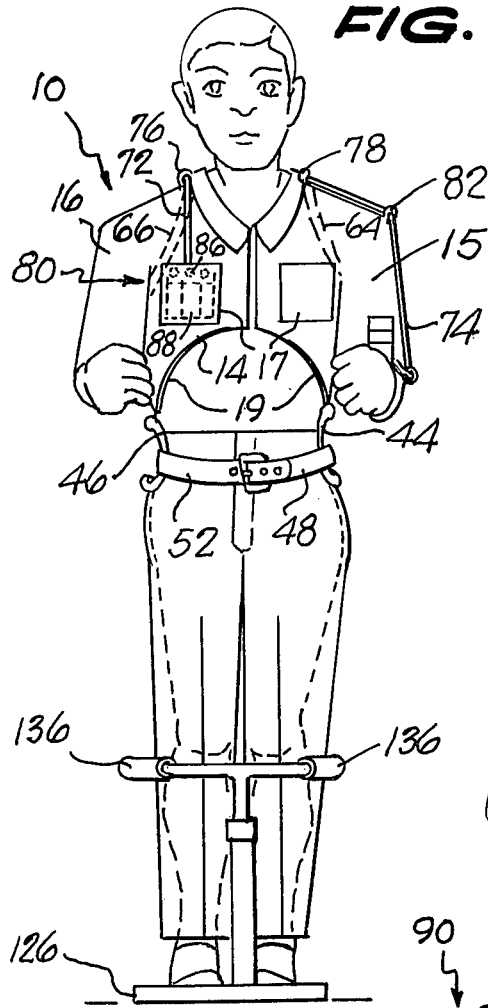
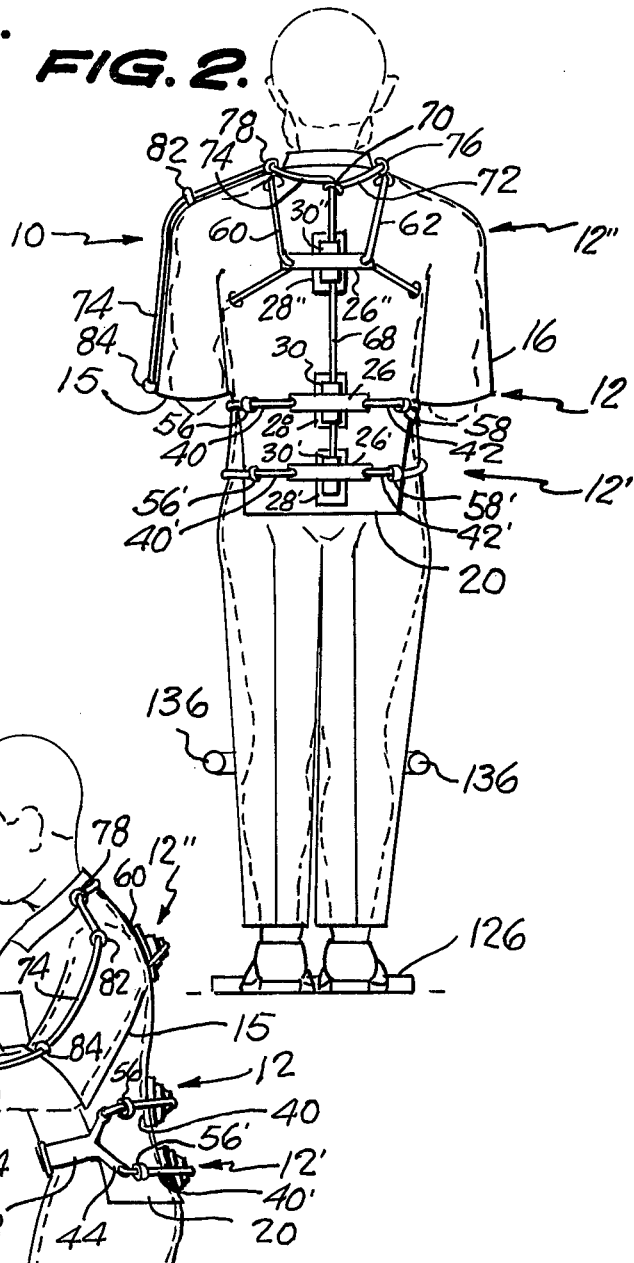
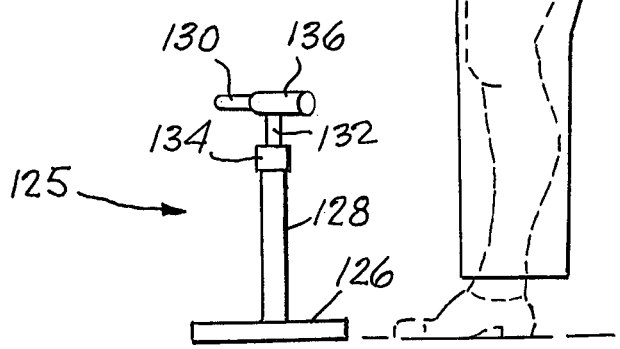

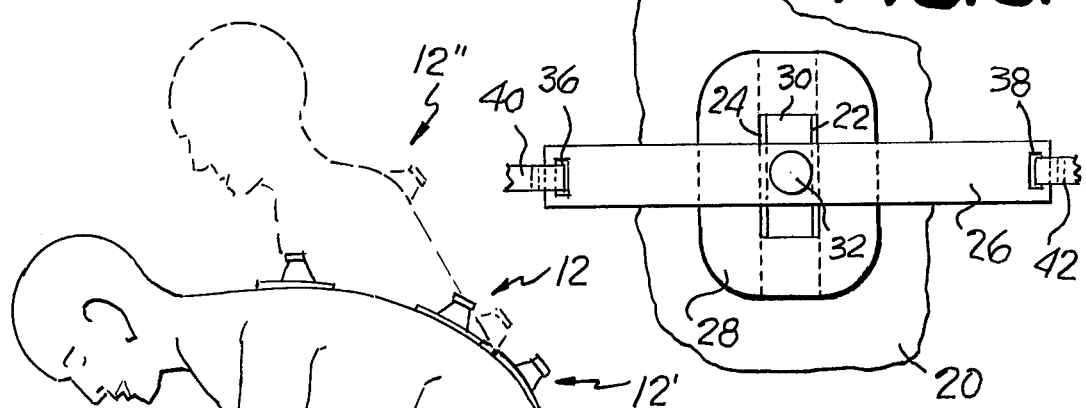

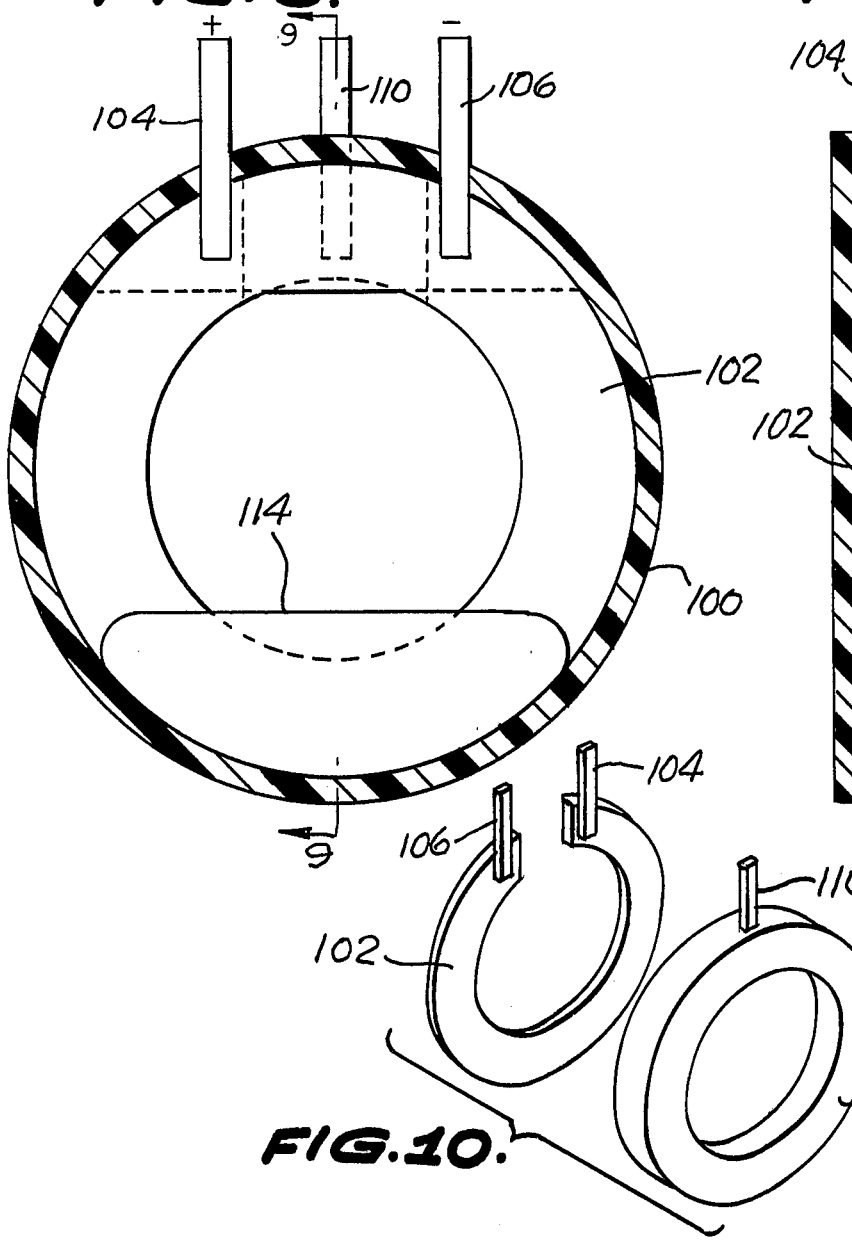
FIG. 8.
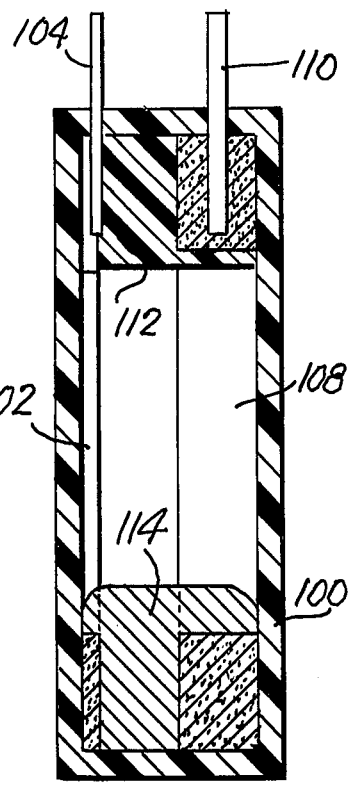
FIG. 9.
FIG. 10.
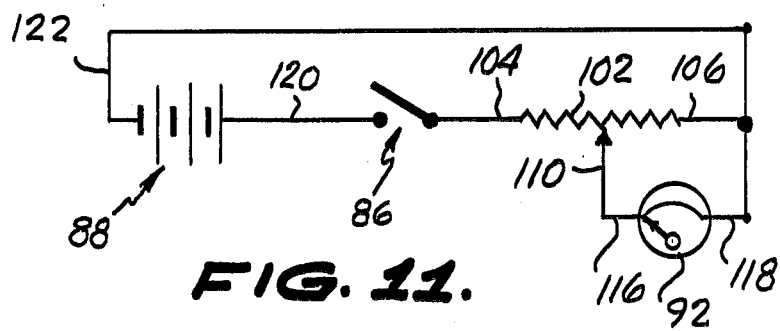
FIG. 11.

STANDARD BENDING PROFILE JACKET

BACKGROUND OF THE INVENTION

1. Field of the Invention

The present invention is related to prophylactic and therapeutic devices for preventing and rehabilitating injury to the back of a human being and, more particularly, is directed towards a jacket in combination with a plurality of novel self-contained electrical measurement devices mounted thereon which is intended to measure the angle of tilt of a plurality of portions of the human spine during an act of leaning.

2. Description of the Prior Art

There are many factors which can contribute to back injury. One prominent factor associates back injury with the physiological failure that can occur during the straightening or unbending of the back in the course of lifting. To be sure, there are many other factors which can contribute to back injury, such as twisting or jerking. Such factors, however, are believed to simply compound the adverse stresses which originate in the bending associated with leaning.

As yet, very little development has taken place in the area of prophylactic devices intended to train an individual to conduct himself in such a manner so as to effectively prevent back injury from occurring. Such a device, if widely utilized, would obviously be extremely useful.

The development of flexural rehabilitation devices for use by individuals with injured backs has also been quite limited. The closest prior art United States patents in this general area of which I am aware include Hall U.S. Pat. No. (3,608,541), Palmer U.S. Pat. No. (3,670,320), and Verhaeghe U.S. Pat. No. (3,582,935). The devices described in the cited patents are, however, quite limited regarding the amount of information they provide. For example, the Hall patent describes a vest-like jacket which comprises a cable that lies along a column adjacent the spine of the wearer. When tensioned as a result of the bending of the wearer's back to a poor posture position, the cable actuates a buzzer by means of the closing of a pair of contacts.

The Palmer and Verhaeghe patents similarly illustrate belt-like posture improving devices which are designed to encircle the waist of the user. If the user allows his stomach muscles to sag or expand, additional tension is placed on the belt segments that results in an electrical circuit being completed to sound an alarm to warn the user that he is standing with incorrect posture.

Each of the foregoing devices is rather limited in its applicability to either prophylactic or rehabilitative programs, in that the only useful information provided by such devices occurs when the wearer slips into a "bad" posture. The devices do not provide any readily measurable or quantitative output indication by means of which the posture of two subjects could be compared, and do not provide any indication of the degree of "good" posture or "bad" posture of the wearer.

It therefore may be appreciated from the foregoing that a device which is intended to be useful as both a rehabilitative and prophylactic tool should preferably provide output information in a substantially continuous fashion, such that the relative flexural conduct of the subject may be monitored, and corrective action taken, on a continuous basis.

Furthermore, such a device should be designed to enable the output readings of a particular individual's flexural conduct to be standardized and thus easily compared with the output readings of a well-known standard, in order to permit mass standardization and utilization, as well as provide a universal tool for the prescribing physician and therapist.

OBJECTS AND SUMMARY OF THE INVENTION

It is therefore a primary object of the present invention to provide an inexpensive, mass-producable device which enables the flexural behavior of an individual to be continuously and accurately monitored.

Another object of the present invention is to provide a device for measuring the flexural conduct of a human being which provides continuous information regarding the dynamics of the entire flexural process.

It a further object of the present invention to provide a standard bending profile jacket which enables easy mounting and use of a plurality of measurement devices, each of which is intended to measure the angle of inclination or tilt of a particular portion of the spine of a human being.

An additional object of the present invention is to provide a device for use in measuring the flexural conduct of the human spine which permits practical field measurement of spinal flexural behavior in order to create a standardized value system which permits qualitative description.

A still further object of the present invention is to provide a device for measuring the flexural conduct of the human spine which, through broad use, can popularize a numerical value measurement system which can lead to less abusive leaning habits.

A still further object of the present invention is to provide a device for measuring the flexural conduct of the human spine which is useful in flexural rehabilitation by providing a standardized numerical goal system towards which the patient and therapist may work.

A still additional object of the present invention is to provide a standard bending profile jacket by means of which the wearer may observe or monitor his or her own flexural style in a continuous fashion.

A still further object of the present invention is to provide a novel variable electrical resistance which is utilized for the purpose of measuring changes in the axial angle of any object to which it is firmly secured.

The foregoing and other objects are attained in accordance with one aspect of the present invention through the provision of apparatus for measuring the flexural conduct of the human spine, which comprises means positioned adjacent a portion of the spine of the user for providing an electrical signal having a magnitude in proportion to the angular inclination of that particular portion of the spine. The electrical signal providing means preferably comprises a potentiometer which is responsive to a change in its angular orientation for providing the continuous electrical output signal.

In accordance with other aspects of the present invention, means are provided for mounting the potentiometer means adjacent the portion of the spine, the mounting means preferably comprising a substantially planar bearing plate positioned against the portion of the spine whose inclination is desired to be monitored. The mounting means further comprises side support means extending from the bearing plate for supporting the potentiometer, and means for uging the bearing plate against the adjacent portion of the spine. The urging means preferably comprises an elongated pressure beam connected to the side support means, and an elastic band which is connected to the respective ends of the pressure beam.

In accordance with yet other aspects of the present invention, a jacket is worn by the user and includes means for guiding the elastic band, and aperture means on the back portion thereof through which the bearing plate extends. Preferably, a plurality of potentiometers are provided which are positioned adjacent a plurality of portions of the spine for respectively providing a plurality of electrical output signals indicative of the angle of tilt of that particular portion of the spine adjacent which they are mounted.

In accordance with yet other aspects of the present invention, a belt may be provided having at least one rear strap connected to one of the plurality of potentiometers, the jacket including means for guiding the strap, the belt including a standard buckle arrangement for attaching same about the waist of the user.

In accordance with more specific aspects of the present invention, the strap means comprises a pair of elastic straps which respectively traverse the lumbar and sacrum portions of the spine, a pair of the potentiometers being connected to the pair of elastic straps at the lumbar and sacrum portions of the spine respectively. The supporting means further comprises a third elastic strap which traverses the thoracic portion of the spine, a third potentiometer being connected thereto thereat.

Means for providing electrical energy are also preferably provided, as are means for indicating the magnitude of each of the electrical signals generated by the potentiometers, as well as means interconnecting each of the plurality of potentiometers with the electrical energy providing means and the indicating means. The indicating means preferably includes means for mounting same about the wrist of the user in order to enable visual observation of same.

In accordance with still other aspects of the present invention, there is provided apparatus for measuring angular changes of a member, which comprises means secured to the member for providing an electrical signal in proportion to the angular inclination thereof. The means preferably comprises potentiometer means responsive to a change in its angular orientation for providing the electrical signal. In a preferred and novel form, the potentiometer means comprises fixed resistance means and fixed conductance means, and movable contact means for establishing an electrical path disposed therebetween. The movable contact means is responsive to gravity to thereby change its point of contact between the resistance means and conductance means as the angular position of the potentiometer means is changed. In a preferred form, the resistance and conductance means are comprised respectively of first and second ring-shaped conductors which are disposed in a spaced substantially parallel relationship. Means are further provided for housing the first and second ring-shaped conductors in a substantially sealed fashion.

More specifically, the first ring-shaped conductor of the preferred potentiometer means comprises a substantially C-shaped main resistance ring having a positive and a negative electrode connected respectively to the ends thereof, while the second ring-shaped conductor comprises a substantially circularly shaped pickup conductance ring having a variance electrode connected thereto. A source of electrical potential is preferably connected between the positive and negative electrodes, while means are connected to the variance electrode for indicating the magnitude of the electrical signal. The movable contact means comprises an electrically conductive fluid which, in a preferred embodiment, comprises mercury.

BRIEF DESCRIPTION OF THE DRAWINGS

The foregoing and other objects, aspects, uses, and advantages of the present invention will become better understood when considered in connection with the following detailed description thereof viewed in conjunction with the accompanying drawings, in which:

FIG. 1 illustrates a frontal, plan view of a preferred embodiment of the standard bending profile jacket of the present invention as worn by an individual subject in a test environment;

FIG. 2 is a back view of the subject illustrated in FIG. 1;

FIG. 3 is a side view of the subject illustrated in FIGS. 1 and 2;

FIG. 4 is a schematic representation of the subject illustrated in FIGS. 1 through 3 while undergoing a test, helpful and understanding the operation of the present invention;

FIG. 5 is a top, plan view which illustrates a preferred embodiment of a clinometer in accordance with the teachings of the present invention;

FIG. 6 is a side view of the preferred embodiment clinometer illustrated in FIG. 5;

FIG. 7 is a plan view, partially broken, which illustrates one preferred embodiment of a means for mounting the clinometers illustrated in FIGS. 5 and 6;

FIG. 8 is a side, plan view of a preferred embodiment of a variable electrical resistance in accordance with the teachings of the present invention;

FIG. 9 is a cross-sectional view of the device illustrated in FIG. 8;

FIG. 10 is an exploded, perspective view illustrating the major components of the device illustrated in FIGS. 8 and 9;

FIG. 11 is a schematic circuit diagram illustrating the operative interconnections for the utilization of the device illustrated in FIGS. 8 through 10; and FIG. 12 is a sectional view of the preferred embodiment of the potentiometer and mounting means of the present invention, and taken along line 12—12 of FIG. 6.

DETAILED DESCRIPTION OF THE PREFERRED EMBODIMENTS

Referring now to the drawings, wherein like reference numerals represent identical or corresponding parts throughout the several views, and more particularly to FIGS. 1 through 3 thereof, a preferred embodiment of the standard bending profile jacket of the present invention, as worn by a user, is indicated generally by the reference numeral 10.

Generally, the jacket 10 includes a front portion 14 which is preferably cut away as at 19 below the breast to eliminate bulk and bunching. The jacket 10 includes a left sleeve 15 and a right sleeve 16, and preferably has a pair of breast pockets 17. The back portion 20 of the jacket 10 preferably extends downwardly in a tapered fashion below the waist to cover the buttocks, as clearly illustrated in FIGS. 2 and 3.

As will become more clear hereinafter, the above-described traditional components of the jacket 10 serve primarily to maintain order between the flexural conduct measuring components. The jacket 10 is preferably comprised of a durable, but inexpensive and easily available, material, and is designed to take advantage of the fact that all individuals know how to put on a jacket and fasten a belt.

The preferred embodiment of the jacket 10 illustrated in FIG. 2 has three clinometer assemblies 12, 12′, and 12″ mounted thereon.

In the preferred mode illustrated, the clinometer assembly 12 is positioned over the lumbar region of the spine, while clinometer assembly 12′ is positioned across sacrum region of the spine, approximately six inches below the lumbar clinometer assembly 12.

The clinometer assembly 12″ is mounted so as to ride the spine between the shoulders next to the thorax. Although particular mounting means are to be described for mounting and positioning the three clinometer assemblies 12, 12′, and 12″, it will be apparent that many equivalent mounting and fastening arrangements are possible.

Referring now to FIGS. 5, 6 and 12, there is illustrated a preferred embodiment of the mounting means for each of the clinometer assemblies. Since each of the mounting assemblies are substantially identical in this preferred embodiment, only a single exemplary structure need be illustrated, that being for clinometer 12. Reference numeral 20 in FIGS. 5, 6 and 12 again indicate the rear portion of the jacket 10 through which each of the clinometer assemblies project.

The clinometer assembly 12 includes a bearing foot 18 which rides directly adjacent that portion of the spine of the user against which the particular clinometer assembly is mounted. The bearing foot 18 preferably comprises an elongate rigid plastic member which projects through a suitably formed aperture in the rear portion 20 of the jacket 10 to ride directly on the spine of the wearer.

Secured to the bearing foot 18 of the clinometer assembly 12 are a pair of spaced, vertically oriented, substantially parallel upstanding side mounting plates 22 and 24, which are shown in FIG. 12 as being of a substantially parallelogram shape. The side mounting plates 22 and 24 serve as a side support means for the electrical measuring device 30 positioned therebetween.

The electrical measuring device 30 positioned between parallel upstanding side mounting plates 22 and 24 preferably comprises a gravity actuated potentiometer, whose particular structure and operation will be set forth in more detail hereinbelow. Suffice it to say that the potentiometer 30 is secured in axial position by a calibrating set screw 32 and functions to deliver an output signal along output leads 33 whose magnitude varies in proportion to the change in its angular position.

Positioned transversely to bearing foot 18 of clinometer assembly 12 is a pressure beam 26 which is connected to the upper edges of side mounting plates 22 and 24. The pressure beam 26 is preferably also formed of a rigid, inflexible plastic member. A pair of apertures 36 and 38 are formed in the respective ends of pressure beam 26. A pair of support straps 40 and 42, which are preferably elastic, extend from the apertures 36 and 38, respectively.

The calibrating set screw 32 extends above the horizontal surface of pressure beam 26, and has a downwardly depending shaft 34 which is positionable against the circumference of potentiometer 30, itself rotatable between plates 22 and 24, so as to act as a set screw type of calibration means.

Finally, a collapsible pressure sponge 28 is interposed between the rear portion 20 of jacket 10 and the pressure beam 26. Pressure sponge 28 is preferably rectangular in shape and is designed to collapse when the clinometer structure is drawn, by means of elastic support straps 40 and 42, so as to bear on the spine of the user through the opening in the jacket 20. The pressure sponge 28 also serves to function of holding the bearing foot 18 against the jacket during non-use, the bearing foot 18 being placed directly adjacent that portion of the spine of the user when pressure is applied to the pressure beam 26, to be explained in more detail hereinafter.

Referring now to FIG. 7, the elastic support straps 40 and 42 of clinometer assembly 12 are seen to be connected between the pressure beam 26 and the upper leg of a pair of V-shaped yoke members 44 and 46, respectively. Connected to the midpoint of yoke 44 is a strap 48 having a standard buckle 50 which cooperates with standard buckle-fastening apertures 54 formed in a receiving strap 52 that is secured to the midpoint of yoke member 46.

Clinometer assembly 12′ is similarly connected to the bottom leg of yoke members 44 and 46 in a fashion directly analogous to that described above in connection with clinometer assembly 12.

Referring back to FIGS. 1 through 3, the relative positioning of the three clinometer assemblies is more clearly illustrated. As described hereinabove, clinometer assemblies 12 and 12′ are each positioned as a portion of a belt assembly which is secured, as seen in FIG. 1, across the abdomen of the user, just below the navel. A pair of loops 56 and 58 are formed in the side seam of the rear portion 20 of jacket 10 through which the elastic straps 40 and 42 of clinometer assembly 12 pass. In a similar fashion, there are provided an analogous pair of loops 56′ and 58′ for elastic straps 40′ and 42′. It can be appreciated that the elastic straps 40, 40′, 42, 42′ simply pass through the loops formed at the side seam of the jacket, there being no further firm attachment to the actual garment 20. It may be appreciated, therefore, that one of the primary functions of the jacket is to simply maintain order between the components during the mounting and dismounting thereof by the wearer.

Clinometer assembly 12″, mounted across the thoracic portion of the spine, has its pressure beam 26″ held in tension by a pair of elastic straps 60 and 62, which pass through apertures formed at the respective ends of pressure beam 26″. As seen in FIG. 2, elastic straps 60 and 62 each extend from the shoulder adjacent the neck of the wearer to a point under the armpit of the wearer, thence being positioned through a pair of channels 64 and 66 formed on the front of the garment which also extend from the shoulder to the armpit, as clearly illustrated in FIG. 1.

The output leads from the potentiometers 30, 30′ and 30″, in clinometer assemblies 12, 12′ and 12″, respectively, are preferably wrapped in a common cable harness 68 which rides up the back portion 20 of jacket 10 through a cable loop 70 positioned just below the neck of the user. The leads from the three potentiometers are then divided into a pair of cables 72 and 74, cable 72 containing the electrical leads for the battery and switch pack 80 and extending through a cable loop 76 formed on the shoulder of jacket 10, while cable 74 contains the output leads of each of the potentiometers and feeds to a bank of output indicators 90.

In order to safely guide cable 74 from shoulder loop 78, a pair of cable loops 82 and 84 are preferably included on the left sleeve 15 of jacket 10. The indicators 90 are preferably comprised of a plurality of gauges 92, 92', and 92", which respectively correspond to clinometer assemblies 12, 12', and 12". The output indicators or meters 92, 92', and 92" are preferably arranged in a stacked fashion such that their output meter readings may be visually observed and compared by the wearer of the jacket. In that regard, they are preferably vertically stacked, one next to the other, as illustrated in FIG. 3, and are mounted to the wrist of the user by a strap 94.

Cable 72 includes a pair of leads from each of the potentiometers and feeds to a battery and switch pack which is indicated generally by the reference numeral 80 (FIG. 1) and which may be stored conveniently in one of the breast pockets 17 of the jacket. Battery and switch pack 80 includes a single switch 86 and a battery 88 for each of the clinometer assemblies 12, 12', and 12".

Referring now to FIGS. 8 through 11, the structure and operation of the novel gravity-actuated potentiometer of the present invention will be described in more detail. Each potentiometer comprises a plastic or glass housing 100 which contains a resistance ring 102 and a conductance ring 108. Resistance ring 102 is substantially C-shaped, and is linear or audio tapered, terminating in a pair of upstanding electrodes 104 and 106, which may be thought of, for the purposes of explanation, as the positive and negative terminals, respectively.

Conductance ring 108 comprises a carbon pick-up ring in the form of a closed circular annulus and having an electrode 110 projecting upwardly therefrom, which electrode serves as the variance terminal.

Resistance ring 102 and carbon pick-up ring 108 are mounted in a substantially parallel spaced relationship within housing 100 by means of a plastic seal and spacer 112 positioned near the terminal portions thereof, as clearly illustrated in FIG. 9.

Positioned at the lowermost portion of housing 100, and bridging the gap between a section of resistance ring 102 and pick-up ring 108 is an electrically conductive material 114, which may, for example, comprise a globule of mercury, which serves as a moving contact for the potentiometer.

There are no moving parts to the potentiometer, other than the mercury globule 114, and the housing 100 may be affixed to any host whose change in axial angle is desired to be monitored.

Referring now to FIG. 11, the electrical circuit connections for each clinometer assembly of the present invention are illustrated. Reference numerals 86 and 88 refer respectively to the switch and battery positioned in pack 80 (FIG. 1), while reference numeral 92 refers to one of the stacked gauges worn on the wrist of the user. Leads 116 and 118 extend from meter 92 to be connected respectively to the variance terminal 110 and the negative terminal 106 of the potentiometer. Negative terminal 106 is connected also to the negative side of battery 88, the positive side 120 thereof being connected to switch 86.

In operation, when switch 86 is closed, and with the potentiometer in a fixed position, a constant amount of current will flow through meter 92 to deflect its needle. If the potentiometer changes its angular inclination, mercury globule 114 will respond so as to either increase or decrease the amount of current fed from variance terminal 110 through meter 92, depending upon the sense of rotation of the potentiometer. In this fashion, the output indication from each potentiometer will comprise an electrical signal whose magnitude will be continuously proportional to its angle of inclination and, hence, will be proportional to the "tilt" or "lean" of the particular portion of the spine adjacent to which the associated potentiometer is positioned. In this manner, the output of each of the potentiometers may be simultaneously compared to obtain a three-digit reading, which may be normalized, to provide an indication of the posture of the three selected portions of the spine at any given instant during the leaning of the subject.

Referring back to FIGS. 1 through 4, a mode of utilization of the jacket 10 of the present invention will now be described. The particular mode of utilization is directed towards a standardization technique whereby the flexural behavior of a large number of people may be compared and standardized. Utilized in conjunction with this technique is a test object which is indicated generally by the reference numeral 125. Test object 125 comprises a horizontal planar base 126, mounted on the ground, which has upstanding therefrom a vertical tubular guide 128. A telescoping post 132 is mounted within vertical tubular guide 128, the vertical position of post 132 being adjustable by means of a height adjusting nut 134. Connected to the top of telescoping post 132 is a horizontally disposed handle 130 to the ends of which are secured a pair of hand grips 136.

In operation, the height of the handle 130 is adjusted to approximately one-fourth of the height of the subject. Standing with the toes at a particular distance from the edge of base plate 126, the subject will lean to grasp the hand grips 136 of handle 130 as illustrated by solid outline in FIG. 4. As the subject bends forward, the pelvic, lumbar and thoracic angles change, as may be seen by comparing the relative position of clinometer assemblies 12, 12', and 12" in dotted outline and in solid outline in FIG. 4. The clinometer frames follow the changes in pelvic, lumbar and thoracic angles, to cause a change in the output electrical signals from the respectively mounted mercury potentiometers. The changing electrical signals are visually observable by means of the gauges 90, which are mounted to permit the subject to directly observe his or her own flexural style.

Alternatively, if a permanent record is desired, a three-pen recorder may be substituted for the wrist gauges. By permanently recording the dynamics of the entire flexural process, it will make it easier to study maximum angles, and will afford an opportunity to study the sequence, or temporal distribution, by which the subject achieves the changes in the entire flexural process.

A comparison of two theoretical outputs of the three clinometer assemblies will demonstrate the value of the present invention. If a subject performs the standardization test as illustrated in FIG. 4, and it results in an output of "20-60-120", it will indicate 100 degrees of total flexure from the lowermost clinometer assembly 12' to the uppermost clinometer assembly 12". It also indicates 40 degrees of lumbar flexure in only six inches of lumbar spine, which could be taken as an indication of "high" flexure.

If a second subject performs the standard lean and it results in output readings of "70-80-100", for example, it will indicate only 30° of total flexure, 10° of flexure being achieved in six inches of lumbar spine. Such a reading may be taken to be a "low" flexure. The reading of "20-60-120" may be qualitatively compared with the reading of "70-80-100", whether they be from the same or different subjects.

It may be appreciated that, for subjects with injured backs, the device will play a useful role in flexural rehabilitation. The subject may, for example, struggle through the recall of voluntary flexural control in an effort to achieve a numerical flexural goal prescribed by a physician or therapist. Once achieved, the subject can rehearse acceptable flexural experience to the point of comfortable rehabilitation, all within the privacy of his home.

When research experience establishes a statistical correlation between flexural style and the incidence of injury to the back, the present invention will be highly useful and a prophylactic tool for preventing back injury.

Obviously, numerous modifications and variations of the present invention are possible in light of the above teachings. It is therefore to be understood that within the scope of the appended claims, the invention may be practiced otherwise than as specifically described herein.

I claim as my invention:

1. Apparatus for measuring the flexural conduct of the human spine, which comprises:

a plurality of gravity responsive potentiometer means each adapted for positioning adjacent a different portion of the spine of the user and each responsive to a change in its angular orientation for providing an electrical signal having a magnitude in proportion to the angular inclination of said portion of the spine; and a plurality of means for respectively mounting each of said plurality of potentiometer means adjacent said different portions of the spine each comprising a bearing plate adapted to be positioned adjacent said portion of the spine, side support means extending from said bearing plate for supporting said potentiometer means, and means for urging said bearing plate against said portion of the spine;

wherein said urging means comprises an elongated pressure beam connected to said side support means, and elastic band means connected to the respective ends of said pressure beam; and means for supporting each of said plurality of means for respectively mounting each of said plurality of potentiometer means.

2. The apparatus as set forth in claim 1, further comprising jacket means worn by the user and including means for guiding said elastic band means, and aperture means on the back portion thereof through which said bearing plates extend.

3. The apparatus as set forth in claim 2, further comprising belt means having at least one rear strap means connected to one of said plurality of potentiometer means, said jacket means including means for guiding said strap means, said belt means including means for selective attachment and removal thereof about the waist of the user.

4. The apparatus as set forth in claim 3, wherein each of said potentiometer means comprises fixed resistance means and fixed conductance means and movable contact means for establishing an electrical path disposed therebetween.

5. The apparatus as set forth in claim 4, wherein said movable contact means is responsive to gravity to thereby change its point of contact between said fixed resistance means and said fixed conductance means as the angular position of said potentiometer means is changed.

6. The apparatus as set forth in claim 5, wherein said fixed resistance means and fixed conductance means respectively, comprise first and second ring-shaped conductors disposed in a spaced substantially parallel relationship.

7. The apparatus as set forth in claim 6, further comprising means for housing said first and second ring-shaped conductors in a substantially sealed fashion.

8. The apparatus as set forth in claim 7, wherein said first ring-shaped conductor comprises a substantially C-shaped main resistance ring having a positive and a negative electrode connected respectively to the ends thereof.

9. The apparatus as set forth in claim 8, wherein said second ring-shaped conductor comprises a substantially circularly shaped pick-up conductance ring having a variance electrode connected thereto.

10. The apparatus as set forth in claim 9, further comprising a source of electrical potential connected between said positive and negative electrodes.

11. The apparatus as set forth in claim 10, further comprising means connected to said variance electrode for indicating the magnitude of said electrical signal.

12. The apparatus as set forth in claim 11, wherein said movable contact means comprises an electrically conductive fluid.

13. The apparatus as set forth in claim 12, wherein said electrically conductive fluid comprises mercury.

14. The apparatus as set forth in claim 1, wherein said supporting means includes belt means selectively positionable about the user and including strap means traversing the back of the user.

15. The apparatus as set forth in claim 14, wherein said strap means is comprised of an elastic material.

16. The apparatus as set forth in claim 14, wherein said strap means comprises a pair of elastic straps which respectively traverse the lumbar and sacrum portions of the spine, a pair of said potentiometer means being connected to said pair of elastic straps at said lumbar and sacrum portions of the spine, respectively.

17. The apparatus as set forth in claim 16, wherein said supporting means further comprises a third elastic strap which traverses the thoracic portion of the spine, a third potentiometer means being connected thereto.

18. The apparatus as set forth in claim 17, wherein said supporting means further comprises a jacket wearable by the user and having a plurality of cutouts on the back thereof through which said plurality of potentiometer means are respectively positionable.

19. The apparatus as set forth in claim 18, wherein said jacket includes means for supporting said elastic straps.

20. The apparatus as set forth in claim 1, wherein each of said plurality of potentiometer means includes movable contact means responsive to gravity for varying its associated electrical signal as the angular position of its associated potentiometer means is.

21. The apparatus as set forth in claim 20, further comprising means for providing electrical energy, means for indicating the magnitude of each of said electrical signals, and means interconnecting each of said plurality of potentiometer means with said electrical energy providing means and said indicating means.

22. The apparatus as set forth in claim 21, wherein said indicating means include means for mounting same about the wrist of the user.

23. The apparatus as set forth in claim 21, wherein said movable contact means comprises an electrically conductive fluid.

24. The apparatus as set forth in claim 23, wherein said electrically conductive fluid comprises mercury.

25. Apparatus for measuring the flexural conduct of the human spine, which comprises:

potentiometer means adapted for positioning adjacent a portion of the spine of the user and responsive to a change in its angular orientation for providing an electrical signal having a magnitude in proportion to the angular inclination of said portion of the spine; and means for mounting said potentiometer means adjacent said portion of the spine comprising a bearing plate adapted to be positioned adjacent said portion of the spine, side support means extending from said bearing plate for supporting said potentiometer means, and means for urging said bearing plate against said portion of the spine;

wherein said urging means comprises an elongated pressure beam connected to said side support means, and elastic band means connected to the respective ends of said pressure beam; and means for supporting said means for mounting said potentiometer means, wherein said supporting means comprises belt means selectively positionable about the user and having said elastic band means connected thereto and adapted to traverse the back of the user.

26. The apparatus as set forth in claim 25, wherein said supporting means further comprises jacket means having means for guiding said belt means.

* * * * *